United States Patent [19]

Staples et al.

[11] Patent Number: 5,728,742
[45] Date of Patent: Mar. 17, 1998

[54] ABSORBENT POLYMERS HAVING A REDUCED CAKING TENDENCY

[75] Inventors: Thomas L. Staples; David E. Henton; Gene D. Rose; Michael A. Fialkowski, all of Midland, Mich.

[73] Assignee: The Dow Chemical Company, Midland, Mich.

[21] Appl. No.: 628,041

[22] Filed: Apr. 4, 1996

[51] Int. Cl.$^6$ ............................ C08J 9/36; B05D 7/00; B05D 3/00
[52] U.S. Cl. .................. 521/57; 427/222; 428/317.9; 521/149
[58] Field of Search .................. 521/57, 149; 428/317.9; 427/222

[56] References Cited

U.S. PATENT DOCUMENTS

| | | |
|---|---|---|
| 4,300,994 | 11/1981 | Liotta . |
| 4,339,373 | 7/1982 | Robinson . |
| 4,490,281 | 12/1984 | James et al. . |
| 4,510,073 | 4/1985 | Hara et al. . |
| 4,734,478 | 3/1988 | Tsubakimoto et al. . |
| 4,997,714 | 3/1991 | Farrar et al. . |

FOREIGN PATENT DOCUMENTS

| | | |
|---|---|---|
| 2147545 | 4/1995 | Canada . |
| 0509708 A1 | 10/1992 | European Pat. Off. .......... C08F 8/14 |

*Primary Examiner*—Morton Foelak

[57] ABSTRACT

The subject invention provides water-swellable polymer compositions having reduced caking tendencies. Such polymer compositions can be produced by employing quaternary ammonium salts. In addition to having reduced caking tendencies such polymers have reduced dust and substantially maintain or increase the surface tension of an aqueous fluid in equilibrium with the polymer and air.

12 Claims, No Drawings

ABSORBENT POLYMERS HAVING A REDUCED CAKING TENDENCY

FIELD OF INVENTION

The subject invention pertains to absorbent polymers whose particles have a reduced tendency to agglomerate in humid environments and/or form dust, a process for the preparation of such polymers, and absorbent articles prepared therefrom.

BACKGROUND AND SUMMARY OF THE INVENTION

Absorbent, i.e., water-swellable, polymers are generally prepared by gel polymerization of a mixture of monomers in aqueous solution. Certain additives, such as crosslinking agents, may be incorporated into the monomer mixture. The product of the polymerization process is then typically dried and subjected to a mechanical means of particle size reduction.

The absorbent polymers are especially useful in many types of personal care devices such as diapers, adult incontinent articles, sanitary napkins, and medical devices because of their ability to readily absorb bodily fluids. Unfortunately, the absorbent polymers also absorb water from the air and when exposed to humid environments the water-swellable polymer particles tend to stick together, i.e., agglomerate or cake, and also tend to stick or adhere to processing equipment. Thus, the polymer particles are not free-flowing, i.e., have poor flowability.

If the polymer particles are not free-flowing then they present a few problems. One problem is that the particles are difficult to incorporate into personal care devices because the reduced flowability hinders the uniform distribution of particles within an absorbent core. Another problem stems from the tendency of the particles to stick to each other and to the manufacturing and processing equipment, e.g., screens, dryers, meters, or fabricating machinery. Production is often hindered because the equipment must be cleaned periodically to remove the agglomerated particles. Yet another problem associated with water-swellable polymer particles that tend to agglomerate is that if the polymer particles have absorbed some water already then the water-swelling capacity for the personal care devices containing said polymer particles may be reduced.

One way in which the caking tendencies of absorbent polymers have been reduced is by blending finely divided silica or fumed silica with the absorbent polymer particles. See U.S. Pat. No. 4,734,478 which mixes 0.01 to 10 parts by weight of finely divided silica with 100 parts by weight of the water absorbent polymer and WO 94/22940 which blends less than 10 percent by weight fumed silica with the water absorbent polymer. Unfortunately, even though the caking tendency of the polymer particles may be reduced, both types of silica are low bulk density solids and tend to add dust into the environment.

Other compounds have been employed to reduce the adhesion tendency of absorbent polymer particles. Among these are nonionic or anionic surfactants. See U.S. Pat. No. 4,286,082 which utilizes the above surfactants in the presence of a crosslinkable monomer to diminish the adhesion of the hydrous polymer to the polymerization vessel. These surfactants may indeed reduce the adhesion tendency of the polymer, but the surfactants also reduce the surface tension of a contacting fluid in equilibrium with the polymer. This is unfortunate in that the surface tension of the contacting fluid is used as a measure of performance of water-swellable polymers.

The surface tension of the contacting fluid in equilibrium is used as a measure of performance because water-swellable polymers which exhibit a higher surface tension generally tend to "wick" better, i.e., the polymer transports aqueous fluids by capillary flow more efficiently and holds the fluids more strongly. As U.S. Pat. No. 5,352,711 discusses, wicking is very important for absorbent devices such as diapers or sanitary articles. The effect of surface tension on capillary flow and capillary pressure is described more fully by the Lucas-Washburn equation as discussed by P. K. Chatterjee, "*Absorbency*", Elsevier, Amsterdam, 1985, pp. 36–37.

Industry would find great advantage in a water-swellable polymer composition which does not agglomerate when exposed to a humid environment, e.g., which comprises more than 90 percent free-flowing polymer particles as measured by the test disclosed herein. Industry would further find advantage in a new process for reducing the agglomeration tendencies of a water absorbent polymer composition which comprises employing liquid anticaking agents rather than solids such as silica which can increase the dust present. Industry would further find advantage if said liquid anticaking agents substantially maintain or increase the surface tension of a contacting liquid in equilibrium with the polymer composition.

Accordingly, in one aspect the subject invention provides a composition comprising a) water-absorbent lightly crosslinked water-insoluble polymer particles; b) an effective amount of an anticaking agent; and optionally c) a hydrophobic or hydrophilic dedusting agent. These compositions comprise more than 75, preferably more than 90, more preferably more than 95, and most preferably more than 99 percent non-caking polymer particles as measured by the test disclosed herein.

In another aspect, the invention also provides a process comprising a) preparing a water-swellable hydrogel by a gel polymerization process; b) drying and sizing the thus prepared hydrogel to obtain a composition comprising dried and sized particles; and c) contacting the composition with an effective amount of an anticaking agent.

Quaternary ammonium salts have been used in conjunction with absorbent gels as a lubricant, in for example, U.S. Pat. No. 4,997,714, but heretofore have not been employed as anti-caking agents.

DETAILED DESCRIPTION OF THE INVENTION

As used herein, the term "substantially maintain or increase the surface tension" means that when an aqueous fluid is in equilibrium with another fluid and the attrition-resistant, water-swellable polymers treated with a hydrophobic dedusting agent of the present invention, the surface tension of the aqueous fluid, as measured by a surface tension test disclosed hereinafter, is decreased by less than about ten percent, preferably less than about five percent, when compared to water-swellable polymers that are not contacted with a hydrophobic dedusting agent. More specifically, the aqueous fluid employed in the surface tension test disclosed herein is a 0.9 percent NaCl solution and the other fluid is air.

As used herein, the term "unassociated dust" means the measurable portion of a water-absorbent polymer particle composition having a maximum diameter less than or equal to 10 microns, which portion is rendered airborne when air is applied to the composition. More specifically, the air is applied and the portion is measured using a pulsed jet disperser described below.

As used herein, the term "physical coating" means that a coating of the anticaking agent and the dedusting agent (if present) in contact with the polymer particles and dust (if present), is not chemically reacted with the polymer, e.g., no covalent surface crosslinking reaction occurs between the anticaking or dedusting agent and the polymer particles or dust.

As used herein, the term "aliphatic hydrocarbon" includes straight or branched chain alkyl, alkenyl, and alkynyl groups which may have linkages such as silicon (—Si—) or oxygen (—O—) within the chain. The aliphatic hydrocarbons may be unsubstituted or substituted with inert substituents.

As used herein, the term "aryl group" includes condensed aromatic rings such as phenyl, naphthyl, phenanthryl, and anthracenyl which are unsubstituted or substituted with inert substituents.

As used herein, the term "inert substituent" means a substituent which is inert, i.e., non-reactive, to its environment. The environment to which the substituent is inert includes the water-absorbent polymer particles and the aqueous liquid in which it is to be dissolved or dispersed. Included among inert substituents are, for example, halogen groups such as fluoro- (—F), chloro- (—Cl), and bromo- (—Br), hydroxy groups (—OH), and alkoxy groups.

The water-swellable or lightly crosslinked hydrophilic polymers that are employable in the present invention can be any of the known hydrophilic polymers which are capable of absorbing large quantities of fluids. In particular, water-absorbent polymers useful in this invention are water-absorbent polymers which contain carboxyl moieties. Preferably, at least about 0.01 equivalent of carboxyl groups are present per 100 grams of the water-absorbent resin.

Among preferred carboxyl-containing water absorbent polymers are hydrolyzates of starch-acrylonitrile graft copolymers, partially neutralized products of starch-acrylic acid or starch-polyvinyl alcohol graft copolymers, saponification products of vinyl acetate-acrylic ester copolymers, derivatives of copolymers of isobutylene and maleic anhydride, hydrolyzates of acrylonitrile copolymers, crosslinked products of hydrolyzates of acrylonitrile copolymers, crosslinked carboxy-methyl cellulose, hydrolyzates of acrylamide copolymers, crosslinked products of hydrolyzates of acrylamide copolymers, partially neutralized products of polyacrylic acids and crosslinked products of partially neutralized polyacrylic acids.

Examples of some suitable polymers and processes, including gel polymerization processes, for preparing them are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; and 4,190,562, which are incorporated herein by reference. Such hydrophilic polymers can be prepared from water-soluble $\alpha,\beta$-ethylenically unsaturated monomers such as monocarboxylic acids, polycarboxylic acids, acrylamide and their derivatives.

Suitable $\alpha,\beta$-ethylenically unsaturated monomers include, for example, acrylic acid, methacrylic acid, crotonic acid, isocrotonic acid and alkali metal salts and ammonium salts thereof; itaconic acid, acrylamide, methacrylamide and 2-acrylamido-2-methyl-1-propane sulfonic acid and its salts. The preferred monomers include acrylic acid and methacrylic acid and their respective salt forms such as alkali metal or ammonium salts.

The water-soluble monomers useful in the present invention may be used in amounts ranging from about 10 percent to about 80 percent by weight based on the total weight of the aqueous monomer solution. Preferably, the amount ranges from about 15 percent to about 60 percent based on the total weight of the aqueous monomer solution.

Optionally, minor amounts of other water-soluble, unsaturated monomers, such as alkyl esters of acid monomers, e.g., methyl acrylate or methyl methacrylate may be present in the water absorbent polymer. In addition, certain grafting polymers, such as, for example, polyvinyl alcohol, starch and water soluble or swellable cellulose ethers may be employed to prepare products having superior properties. Such grafting polymers, when employed, are used in amounts up to about 10 weight percent based on the $\alpha,\beta$-ethylenically unsaturated monomer. Further, it may be advantageous to include a chelating agent to remove trace metals from solution, e.g., when a metal reaction vessel is employed. One such chelating agent is VERSENEX™ V-80 (an aqueous solution of the pentasodium salt of diethylenetriamine pentaacetic acid) (Trademark of The Dow Chemical Company). Such chelating agents, when employed, are generally used in amounts between about 100 and about 2000 ppm based on the $\alpha,\beta$-ethylenically unsaturated monomer.

It is desirable to obtain a level of conversion of monomer to polymer of at least about 95 percent. The polymerization may be carried out using acid monomers that are not neutralized or that have been neutralized or partially neutralized prior to the polymerization. Neutralization is conveniently achieved by contacting the aqueous monomer with an amount of basic material sufficient to neutralize between about 20 and about 95 percent of the acid groups present in the acid monomers. Preferably, the amount of basic material will be sufficient to neutralize between about 40 percent and 85 percent, and most preferably between about 55 percent and about 75 percent of the acid groups present in the acid monomers. When pre-neutralizing the monomer solution, it is important to control the neutralization conditions so that the heat of neutralization does not cause the premature polymerization of the monomer mixture. The neutralization is advantageously carried out at temperatures below about 40° C., preferably at temperatures below about 35° C.

Compounds which are useful to neutralize the acid groups of the monomer are typically those which will sufficiently neutralize the acid groups without having a detrimental effect on the polymerization process. Such compounds include alkali metal hydroxides, and alkali metal carbonates and bicarbonates. Preferably, the material used to neutralize the monomer is sodium or potassium hydroxides or carbonates. In determining the desired degree of neutralization, care must be taken to ensure that the pH of the resulting crosslinked absorbent polymer, which will be contacted with or dispersed in an aqueous fluid to be absorbed, is maintained in a range appropriate for the applications for which the polymer is intended. Alternatively, the polymerization may be carried out employing unneutralized monomers and thereafter neutralizing, as is known in the art.

Conveniently, a conventional vinyl addition polymerization initiator is used in the polymerization of the water-soluble monomers and the crosslinking agent. A free radical polymerization initiator which is sufficiently soluble in the monomer solution to initiate polymerization is preferred. For example, water soluble persulfates such as potassium persulfate, ammonium persulfate, sodium persulfate, and other alkali-metal persulfates, hydrogen peroxide and water soluble azo-compounds such as 2,2'-azobis (2-amidinopropane.HCl) may be used. Some of these initiators, such as hydrogen peroxide, can be combined with reducing substances such as sulfites or amines to form known redox initiator systems. The total amount of initiators used may range from about 0.01 to about 1.0 weight percent, preferably about 0.01 to about 0.5 weight percent, based on the total weight of $\alpha,\beta$-ethylenically unsaturated monomer reactants.

The water-absorbent resin will preferably be lightly crosslinked to render it water-insoluble and water-swellable. The desired crosslinked structure may be obtained by the copolymerization of the selected water-soluble monomer and a crosslinking agent possessing at least two polymerizable double bonds in the molecular unit. The crosslinking agent is present in an amount effective to crosslink the water-soluble polymer. The preferred amount of crosslinking agent is determined by the desired degree of absorption capacity and the desired strength to retain the absorbed fluid, i.e., the desired absorption under load (AUL). Typically, the crosslinking agent is used in amounts ranging from about 0.0005 to about 5 parts by weight per 100 parts by weight of $\alpha,\beta$-ethylenically unsaturated monomer used. More preferably, the amount ranges from about 0.1 to about 1 part by weight per 100 parts by weight of the $\alpha,\beta$-ethylenically unsaturated monomer. Usually, if an amount over about 5 parts by weight of crosslinking agent per 100 parts is used, the resulting polymer has too high a crosslinking density and exhibits a reduced absorption capacity and increased strength to retain the absorbed fluid. If the crosslinking agent is used in an amount less than about 0.0005 part by weight per 100 parts, the polymer usually has too low a crosslinking density, and when contacted with the fluid to be absorbed becomes sticky and exhibits a lower initial absorption rate.

While the crosslinking agent will typically be soluble in the aqueous solution of the $\alpha,\beta$-ethylenically unsaturated monomer, the crosslinking agent may be merely dispersible in such a solution, without negative implications. The use of such dispersing agents is disclosed in U.S. Pat. No. 4,833, 222, incorporated herein by reference. Suitable dispersing agents include carboxymethyl cellulose suspending aids, methyl cellulose, hydroxypropyl cellulose, and polyvinyl alcohol. Such dispersing agents are typically provided at a concentration between about 0.005 and about 0.1 weight percent, based on the total weight of $\alpha,\beta$-ethylenically unsaturated monomer reactants.

Typical crosslinking agents include monomers having in one molecule 2 to 4 groups selected from the group consisting of $CH_2=CHCO—$, $CH_2=C(CH_3)CO—$ and $CH_2=CH—CH_2—$. Exemplary crosslinking agents are diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; highly ethoxylated trimethylol propane triacrylate; tetracrylate and tetramethacrylate of pentaerythritol; and tetraallyloxyethane.

As noted in WO 93/05080, published on Mar. 18, 1993, incorporated herein by reference, certain crosslinking agents yield particularly preferred absorptive properties. Such preferred crosslinking agents include methylenebisacrylamide, bis(acrylamido)acetic acid and its salts, allyl acrylate, allyl methacrylate, and esters or amides having both a vinyl and an allyl functionality. Other particularly preferred crosslinking agents and methods include those disclosed in WO 94/20547, published on Sep. 15, 1994, incorporated herein by reference. Such preferred crosslinking agents include mixtures of polyvinyl compounds such as, for example, highly ethoxylated trimethylolpropane triacrylate and allyl methacylate, and polyglycols such as, for example, polyethylene glycol.

In a preferred embodiment for making polymers useful in the practice of this invention, an aqueous solution of the $\alpha,\beta$-ethylenically unsaturated monomer in the partially neutralized form, the crosslinking agent, the initiator and a grafting polymer substrate, if desired, is prepared.

The polymerization of the mixture may be initiated by elevating the temperature of the mixture containing the initiator or by using a redox-type initiator as described above. Generally, the temperature at which polymerization will begin ranges from about 20° C. to about 45° C. The temperature at which the polymerization is carried out is highly dependent on the type of monomers used and the specific initiator system employed. Preferably, the maximum temperature of polymerization ranges from about 50° C. to about 100° C., most preferably from about 60° C. to about 100° C. The method by which the temperature of the polymerization is controlled is not critical so long as sufficient cooling is present to remove a sufficient amount of the heat which is generated during polymerization so as to limit the maximum temperature.

The resultant polymer is typically pre-sized and dried using means well-known in the art. Suitable drying means include fluidized bed driers, rotary driers, forced air ovens, through-circulation band driers, etc. In some instances, drying will occur in two or more stages, i.e., multi-stage drying. In multi-stage drying, the pre-sized polymer particles are partially dried in the initial stage or stages, e.g., the pre-sized polymer particles are dried to less than about 30, preferably less than about 20 percent moisture level. Drying to less than about 10, preferably less than about 5 percent moisture level is accomplished during the completion of drying stages. During the initial stage or stages of drying, the pre-sized particles typically fuse together into sheets. Following the completion of drying, the polymer is more completely sized to form particles having an average diameter less than about 0.8 mm. During such sizing, dust, characterized by extremely small particle sizes may result, i.e., particle sizes less than or equal to 10 microns. The amount of dust generated will vary based on manufacturing procedures.

To improve absorptive properties, the dried particles may be heat treated in accordance with the procedures set forth in WO 93/05080, published on Mar. 18, 1993 and/or WO 94/20547, published on Sep. 15, 1994, incorporated herein by reference. In particular, the dried particles are heated for a time sufficient to increase the modulus, centrifuge capacity, and/or the absorbency under load. An oxidizing agent, such as a bromate, chlorate, chlorite, or mixture thereof, may be uniformly distributed within the water absorbent polymer prior to such heat treatment to enhance one or more of the preceding properties. Such heat treatment is preferably carried out at a temperature of at least about 170°, more preferably of at least 180°, and most preferably of at least about 190° C. Such heat treatment is preferably carried out at a temperature of less than about 250°, more preferably less than about 240° C.

The time period for heat treatment should be sufficient to effect an improvement in absorptive properties. The exact times of heat treatment required will be affected by the equipment chosen, and can be determined empirically by examination of product properties. Preferably, the time is at least about 3 minutes, and more preferably at least about 5 minutes. If the time is too long, the process becomes uneconomical and a risk is run that the absorbent resin may be damaged. Preferably, the maximum time of heating is about 150 minutes or less, more preferably 60 minutes or less.

The method of heat treatment is not critical. For example, forced air ovens, fluidized bed heaters, heated screw conveyors, and the like may be successfully employed. If desired, the heated polymer may be remoisturized for ease in handling. While such remoisturization may serve to decrease the amount of unassociated dust, it may lead to clumping of the polymer product.

Another way to improve absorptive properties of the polymer particles may be to surface crosslink the polymer particles. Procedures for surface crosslinking are well known in the art and described in, for example, DE 4244548, DE 4020780, EP 605150, and U.S. Pat. Nos. 4,734,478 and 4,666,983. These procedures, like heat treatment, may increase the modulus, centrifuge capacity, and/or the absorbency under load of the polymer particles.

The dried, sized and optionally heat-treated or optionally surface crosslinked polymer particles are then contacted with an effective amount of an anticaking agent. It is critical that the polymer particles not be in the form of a gel, i.e., have less than about 30, preferably less than about 20, more preferably less than about 10 weight percent water, before contacting them with the anticaking agent. If the anticaking agent is contacted with a gellular form of polymer particles then the anticaking agent is likely to combine with water and be absorbed further into the interior of the polymer particles. If this occurs then the anticaking properties of the particles are reduced because the anticaking agent is not at the surface of the particles.

It is also critical to this invention that the polymer particles not be subjected to temperatures above about 100° C. after the particles are contacted with the anticaking agent. This is due to the fact that the anticaking agent may vaporize or degrade at higher temperatures. Therefore, if a drying step and/or a heat treatment step is to be undertaken which will subject the particles to temperatures above about 100° C., then the drying and/or the heat treatment steps should be accomplished before the particles are contacted with the anticaking agent.

The anticaking agent physically coats the polymer particles and serves to diminish the adhesion of the polymer particles to each other and to machinery or vessels with which the polymer particles come into contact. The polymer particles will not suffer significant decreases in flowability nor undergo significant caking upon moisture absorption. After contact with an effective amount of anticaking agent at least about 75, preferably at least about 90, more preferably at least about 95, most preferably at least 99 percent of the particles should be non-caking polymer particles according to the test disclosed herein entitled "Caking Test."

As defined herein, the term "effective amount of an anticaking agent" means an amount of a cationic surfactant, for example, a sulfonium, phosphonium, or quaternary ammonium compound, which, when applied to the polymer particles, renders at least about 75, preferably at least about 90, more preferably at least about 95, most preferably at least about 99 percent of the particles non-caking according to the "Caking Test." Although this effective amount will vary depending upon the polymer, the anticaking agent, and the amount of moisture, typically the amount is at least about 100, preferably at least about 500, more preferably at least about 1000 parts per million of anticaking agent based on the weight of the polymer particles. Typically, this amount is at most about 5000, preferably at most about 4000, more preferably at most about 3000 parts per million of anticaking agent based on the weight of the polymer particles.

Preferably, the cationic surfactants useful as anticaking agents are quaternary ammonium salts which are represented by the formula 1:

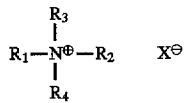

wherein $R_1$ and $R_3$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; $R_2$ is a $C_1$–$C_6$ aliphatic hydrocarbon or a phenyl group; and $R_4$ is a $C_1$–$C_{22}$ aliphatic hydrocarbon, a $C_1$–$C_4$ aliphatic hydrocarbon substituted with an unsubstituted aryl, or a $C_1$–$C_4$ aliphatic hydrocarbon substituted with an aryl group substituted with a $C_1$–$C_{22}$ aliphatic hydrocarbon, or $R_4$ is a radical represented by the formula 2:

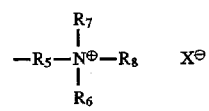

wherein $R_5$ is a $C_2$–$C_6$ alkylene group; $R_6$ is a $C_1$–$C_6$ aliphatic hydrocarbon or a phenyl group; $R_7$ and $R_8$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; or $R_2$ and $R_4$ taken together with the nitrogen atom forms a ring selected from the group consisting of pyrrolidine, pyrroline, pyrrole, pyrazole, triazole, indole, piperazine, piperidine, morpholine, and hexahydroazepine; or $R_1$, $R_2$, and $R_4$ taken together form a ring selected from the group consisting of pyridinium and imidazolinium; and $X^\ominus$ is an anion; with the provisos that if $R_4$ is not the radical represented by formula 2 then the sum of the carbons in $R_1$, $R_2$, $R_3$, and $R_4$ must be at least 15 and if $R_4$ is the radical represented by formula 2 then at least one of $R_1$, $R_3$, $R_7$, and $R_8$ must have 8 or more carbon atoms.

A preferred embodiment is the above formula in which $R_1$ is an aliphatic hydrocarbon having at least 16 carbon atoms such as hexadecyl, octadecenyl, octadecyl, docosanyl, docosenyl, and natural product derivatives such as tallow, soya, and rape seed; $R_2$ is an alkyl group having one to six carbons such as methyl, ethyl, 2-hydroxyethyl, 3-hydroxypropyl, 2-(2-hydroxyethyloxy)ethyl, or 3-(3-hydroxypropyloxy)-propyl; and $R_3$ and $R_4$ are independently an alkyl group having one to six carbons such as methyl, ethyl, 2-hydroxyethyl, 3-hydroxypropyl, 2-(2-hydroxyethyloxy)ethyl, or 3-(3-hydroxypropyloxy)-propyl or an alkyl group having one to four carbon atoms substituted with a phenyl such a benzyl or phenethyl group.

Another preferred embodiment is the above formula in which $R_1$ and $R_3$ are independently an aliphatic hydrocarbon having at least eight carbon atoms such as octyl, decyl, dodecyl, tetradecyl, hexadecyl, octadecenyl, octadecyl, docosanyl, docosenyl, or natural product derivatives such as tallow, soya, and rape seed; $R_2$ is an alkyl group having one to six carbon atoms such as methyl, ethyl, 2-hydroxyethyl, 3-hydroxypropyl, 2-(2-hydroxyethyloxy)ethyl, or 3-(3-hydroxypropyloxy)propyl; and $R_4$ is an alkyl group having one to six carbons such as methyl, ethyl, 2-hydroxyethyl, 3-hydroxypropyl, 2-(2-hydroxyethyloxy)ethyl, or 3-(3-hydroxypropyloxy)-propyl or an alkyl group having one to four carbon atoms substituted with a phenyl such a benzyl or phenethyl group.

Yet another preferred embodiment is the above formula wherein $R_4$ is the radical represented by formula 2; $R_1$ is an aliphatic hydrocarbon having at least eight carbon atoms such as octyl, decyl, dodecyl, tetradecyl, hexadecyl, octadecenyl, octadecyl, docosanyl, docosenyl, or natural product derivatives such as tallow, soya, and rape seed; $R_2$ and $R_6$ are independently an alkyl group having one to six carbon atoms such as methyl, ethyl, 2-hydroxyethyl, 3-hydroxypropyl, 2-(2-hydroxyethyloxy)ethyl, or 3-(3-hydroxypropyloxy)-propyl; $R_5$ is a $C_2$–$C_6$ alkylene such as ethylene, propylene, or butylene; and $R_3$, $R_7$ and $R_8$ are independently a $C_1$–$C_{22}$ aliphatic hydrocarbon such as methyl, ethyl, 2-hydroxyethyl, 3-hydroxypropyl, 2-(2-hydroxyethyloxy)ethyl, or 3-(3-hydroxypropyloxy)-propyl, octyl, decyl, dodecyl, tetradecyl, hexadecyl, octadecenyl, octadecyl, docosanyl, docosenyl, or natural product derivatives such as tallow, soya, and rape seed or alkyl groups having one to four carbon atoms substituted with a phenyl such as benzyl or phenethyl.

Preferably, $X^\ominus$ is a halide such as chloride ($Cl^\ominus$) or a methyl sulfate group ($MeSO_4^\ominus$).

For ease of contacting the anticaking agent with the polymer particles, it is preferable to utilize the anticaking agent in a liquid form. Because the quaternary ammonium salts used as anticaking agents have relatively low melting points, the anticaking agent may simply be heated above its melting point to form a liquid which is then applied to the polymer. However, if heat is employed then the temperature should not be raised above the anticaking agent's boiling point. For this reason, it may be more preferable to dissolve the anticaking agent in a solvent which is a liquid at room temperature. Although not required, it may be advantageous if the solvent which is employed is readily removed from the polymer particles, e.g., by evaporation. In this manner solvents which may affect the surface tension of an aqueous fluid in equilibrium with the polymer can be removed and the surface tension can be substantially maintained or increased. Useful solvents include such compounds as water, alcohols, ethers, ketones, and mixtures thereof.

A particularly preferred embodiment may be to utilize the hydrophilic dedusting compounds of WO 94/22940, incorporated herein by reference, as solvents. By employing hydrophilic compounds of WO 94/22940, such as polyether polyols, as solvents, one may obtain an anticaking compound which also has reduced dust. The solvent should be employed in an effective amount to serve as a dedusting agent as defined below. The hydrophilic dedusting compound may be employed in amounts which do not substantially affect the surface tension of an aqueous fluid in equilibrium with the polymer and air or in greater amounts if the hydrophilic dedusting compound readily evaporates.

Another particularly preferred embodiment may be to utilize hydrophobic compounds as solvents or as co-solvents with the hydrophilic compounds. Hydrophobic compounds disclosed below serve as dedusting agents while substantially maintaining or increasing the surface tension of an aqueous fluid in equilibrium with the polymer and air. Exemplary hydrophobic compounds often include aliphatic hydrocarbon oils, such as as mineral oil, and alkanes or alkenes having between about 7 and about 18 carbon atoms optionally substituted with OH, $CO_2H$ or esters thereof. Natural oils such as castor, corn, cottonseed, olive, rapeseed, soybean, sunflower, other vegetable and animal oils, as well as esters, alcohols, and acids of the oils are useful in the invention as well as silicone oils of similar viscosities. When hydrophobic compounds are employed as solvents they should be employed in an effective amount to serve as a dedusting agent as defined below.

If a solvent for the anticaking material is employed which does not also serve as a dedusting agent, or if no solvent is employed, then it may be desirable to contact the dried and optionally heat treated or optionally surface crosslinked particles with an effective amount of a dedusting agent. The contacting with the dedusting agent may be employed either before, after, or simultaneously as the anticaking agent. The dedusting agent will serve to adhere the dust to the larger polymer particles or to the walls of the mixing vessel or container in which the polymer is retained during handling, which will translate to reduced levels of unassociated dust in the finished polymer product at the various stages of handling. Moreover, the application of the dedusting agent to the polymer samples does not substantially detrimentally affect the performance or properties of the polymer.

Useful dedusting agent agents are hydrophilic compounds such as those disclosed in WO 94/22940, e.g. polyether polyols, and hydrophobic compounds such as aliphatic hydrocarbon oils, such as as mineral oil, and alkanes or alkenes having between about 7 and about 18 carbon atoms optionally substituted with OH, $CO_2H$ or esters thereof. Natural oils such as castor, corn, cottonseed, olive, rapeseed, soybean, sunflower, other vegetable and animal oils, as well as esters, alcohols, and acids of the oils are useful as well as silicone oils of similar viscosities. The above compounds may be employed in purified form, in solutions, or in mixtures.

As defined herein, the term "effective amount of a dedusting agent" or "effective amount to serve as a dedusting agent" means an amount of a material which, when applied to the polymer material, reduces the concentration of unassociated dust having a diameter of less than 10 microns by at least about 80, preferably at least about 90, more preferably by at least about 95, and most preferably by at least about 99 percent and/or which produces dedusted compositions comprising less than about 7, preferably less than about 5, more preferably less than about 2.5 ppm unassociated dust having a maximum diameter less than or equal to 10 microns. This amount will vary based upon the amount of dust initially present, the type of water-absorbent polymer, and the dedusting agent employed. Generally, the amount of dedusting agent is at least 100, preferably at least 200, more preferably at least 300 ppm based on the weight of the polymer particles. The amount is generally, less than 4000, preferably less than 2000, more preferably less than 1000 ppm based on the weight of the polymer particles.

As mentioned above, if a dedusting agent is to be employed then the dried, sized and optionally heat treated or optionally surface crosslinked polymer particles may be contacted with the dedusting agent either before, after or simultaneously as the contact with the anticaking agent. The dedusting agent may also be employed as a solvent for the anticaking agent. In any event, both the anticaking agent and the dedusting agent should be contacted with the polymer particles under conditions such that the particles can be easily coated with the agents. Preferably, such contacting will be conducted by spraying the agents onto the polymer or immersing the polymer in the agent followed by some form of mechanical distribution, such that adequate distribution of the agent or agents on the water-absorbent resin particles occurs. If spraying then it may be preferable to utilize an air atomizing nozzle and mix a fluidizing amount of water with the agent or agents to better distribute the agent. Typically, the amount of water is less than about 5, preferably less than 4, more preferably less than 3 weight percent based on the weight of the agents. The amount of water is more than 1, preferably more than 2 weight percent based on the weight of the agents. Examples of blending equipment/processes include simple tumbling of a jar, or blending in a conical dryer, ribbon blender, drum tumbler, paddle blender etc. Moderate stirring, shaking, or even a short distance of conveying in a screw-conveyer can be sufficient for such adequate distribution of the agent or agents over the particles, particularly if the particles are at an elevated temperature. Moderate grinding will also suffice, but is not necessary. The type of contacting employed may be the same or different for the anticaking agent and the dedusting agent if the polymer particles are contacted with the anticaking agent and dedusting agent at separate times.

The temperature of contacting the agents can be any temperature at which the agent does not evaporate, solidify, become too viscous, or significantly react with the carboxyl moieties of the absorbent resin polymer. Such temperatures are typically from about 20° to about 150° C., preferably from about 20° to about 60° C. It should be noted that elevated temperatures, i.e., those above ambient temperature, i.e., above about 25° C., improve the speed of coating of the particles. However, if the temperature employed is between about 100° C. and about 150° C. then the time of contacting should not be so long that the agents degrade. Typically, if the temperature remains elevated for less than about 5 minutes, preferably less than about 3 minutes, no significant degradation will occur.

The superabsorbent polymers of this invention are useful in the manufacture of moisture absorbent articles, such as disposable diapers, sanitary napkins, incontinence garments, bandages, and the like. The superabsorbent compositions of this invention are particularly useful in the manufacture of thin and ultra thin disposable diapers which have excellent moisture absorbence capacity, fluid distribution properties and reduced leakage.

In making absorbent articles with the compositions of this invention, the superabsorbent composition may be mixed with, attached to, layered in, or dispersed in a porous matrix of fibers. Such matrices are made with hydrophilic fibers such as wood pulp or fluff, cotton linters, and synthetic fibers or a mixture of the fibers and the wood fluff. The fibers can be loose or joined as in nonwovens. The synthetic fibers can be polyethylene, polypropylene, polyesters, copolymers of polyesters and polyamides and the like. The synthetic fibers may be meltblown fibers or fibers which have been treated to render them hydrophilic. Additionally, the superabsorbent polymers of the invention may be incorporated in the absorbent article in a compartment or localized area of the absorbent structure.

Absorbent articles, such as disposable diapers, are made with a liquid-impermeable backing material, a liquid-permeable bodyside facing material and the liquid-absorbing composite sandwiched between the backing material and the facing material. The liquid-impermeable backing material can be made from commercially available polyolefin film and the liquid-permeable facing material can be made from a commercially available nonwoven material, such as spunbonded or corded fibrous web which is wettable and capable of passing urine.

The absorbent articles of the invention may comprise from about 5 percent to about 95 percent by weight of the superabsorbent polymers of the invention. In a typical absorbent article, the superabsorbent polymer of the invention may be dispersed in a fiber matrix in which the superabsorbent is present in an amount from about 30 to 70 weight percent and the fiber matrix comprising 70 to 30 weight percent of the article. In another form of absorbent article, the superabsorbent may be present in a containment structure in which the superabsorbent polymer is present in an amount of about 30 to 95 percent by weight. Combinations of dispersed superabsorbent polymer and contained superabsorbent polymer are also known.

The superabsorbent polymers of this invention can be used in the manufacture of absorbent articles such as those described in U.S. Pat. Nos. 3,669,103; 3,670,731; 4,654,039; 4,699,823; 4,430,086; 4,973,325; 4,892,598; 4,798,603; 4,500,315; 4,596,567; 4,676,784; 4,938,756; 4,537,590; 4,935,022; 4,673,402; 5,061,259; 5,147,343; 5,149,335; and 5,156,902; the teachings of which are hereby incorporated by reference.

The process used to measure the amount of caking at a particular moisture level is called the "Caking Test". Utilization of this test allows one to determine the effectiveness of an anticaking agent by determining the amount of moisture a sample may absorb and still be free-flowing. The test involves placing a desiccator, for example a Cole-Parmer catalog #G-08904-00, into an oven. The desiccator is maintained at 80 percent humidity by placing a straight sided evaporation dish containing a saturated solution of potassium bromide inside the dessicator. The oven is maintained at 40° C. Five gram samples of each dried, i.e., less than about 5 percent water by weight, superabsorbent polymer to be tested are placed in an aluminum foil pan or plastic weigh dish measuring 6 centimeters in diameter and 1.5 centimeters deep. The pan is removed from the dessicator after an amount of time sufficient for the samples to reach the desired moisture level to test. The samples are weighed to determine the moisturized mass and then allowed to cool to room temperature. While slightly agitating, for example by lightly tapping, the sample is screened through a No. 8 U.S.A. Standard Testing Seive (2.36 millimeters). The amount which passes through the sieve is weighed to determine the mass of the non-caking polymer particles. The percent of the particles which are non-caking is then determined by the following formula: Non-caking percent=(mass of non-caking polymer particles/moisturized mass)×100. The moisture level in percent may be determined by the following formula [(moisturized mass−weight of initial sample)/weight of initial sample)]×100.

The process for measuring the amount of unassociated dust having a diameter less than a predetermined size present in a water-swellable polymer composition, i.e., "Dust Test," is described below. In the case of the Examples, the measurement process was used to determine the amount of unassociated matter having a maximum size less than or equal to 10 microns. The process is applicable, however, to measure the amount of unassociated dust having a diameter less than other predetermined sizes, the predetermined sizes typically consistent with either the manufacturer's or the purchaser's specifications. The process comprises:

(a) placing the composition into the sample holder of a pulsed jet disperser;

(b) blasting the composition with air dried by passage through dehydration means; and (c) determining the weight of particles in each of a plurality of size increments.

Dehydration means are suitable to reduce the amount of water present in the air to be used to blast the polymer composition. Suitable dehydration means include molecular sieve cartridges, dessicating materials, membranes, etc. An especially preferred dehydration means is a molecular sieve cartridge.

The dust levels of the coated samples may be measured as follows. Approximately 0.01 to 0.2 grams of the sample to be tested is placed in the sample holder of a pulsed jet disperser, for example an AEROSIZER™ available from Amherst Process instruments (Hadley, Mass.). The pulsed jet disperser is fitted with a 250 micron screen to prevent particles greater than 250 microns in diameter from entering the detector. The air delivered to the pulsed jet disperser is filtered using the factory supplied filter and is dried using a molecular sieve cartridge. The samples are blasted with the dried air, with the exhaust stream being directed to the detector and analyzed until the instantaneous count rate decays to less than 20 particles per second on the low sensitivity setting of the detector.

Measurements are made on separate portions of the samples and are averaged. For each portion, a determination is made of the total number of particles in each of 500 size increments evenly distributed logarithmically from 0.2 to 200 microns, the instrument exhibiting an approximate lower level of detection of 0.5 microns. The weight of material in each of these size increments is calculated using the following formula (3):

Weight=(number of particles in an increment)(density)($\pi$)(particle diameter)$^3$/6.     (3)

For sodium polyacrylate superabsorbent materials, the density is assumed to be 1.60 g/cm$^3$.

The aggregate weight of unassociated material less than 10 microns is designated weight$_{dust}$. This weight is compared to the weight of sample originally introduced into the disperser, i.e., weight$_{sample}$. The percent dust is determined in accordance with equation (4):

Weight percent dust (%)=100(weight$_{dust}$)/(weight$_{sample}$).     (4)

The test to measure the surface tension, i.e., "Surface Tension Test," utilizes a Du Noüy tensiometer, for example, a Processor Tensiometer K12™ from Krüss. The preparation of an aqueous fluid to be measured, in equilibrium with the absorbent polymer and air, has been substantially adapted from U.S. Pat. No. 4,654,039. One gram extracts of each of the above absorbent polymers, i.e., the control (untreated) absorbent polymer and the absorbent polymer treated with hydrophobic dedusting agents, is shaken with 200 grams of a 0.9 weight percent NaCl solution to simulate a urine solution. The surface tension is then measured with the tensiometer.

EXAMPLE 1

A test is conducted to examine the non-caking percent, moisture level in percent, and dustiness of water-swellable polymers and the surface tension of a liquid in contact with said polymers.

A water-swellable polymer is obtained which has been dried to about 5 percent moisture. The polymer is DRYTECH™ 2035 superabsorbent (available from The Dow Chemical Company), a heat-treated, 62 percent neutralized polyacrylate. A predetermined amount of anticaking agent, as shown in Table I, dissolved in isopropyl alcohol except where indicated, is added dropwise to samples of the polymer at 25° C. The coated particles are then rolled for 60 minutes to distribute the agent on the particle surfaces. The non-caking percent and moisture level (in percent) during the Caking Test is measured as described in the Caking Test above. The amount of dust below 10 microns is measured as described in the Dust Test above. The surface tension is measured as described in the Surface Tension Test above. The results with respect to each sample is set forth in Table I. Table IA describes the surfactants used as anticaking agents exemplified in Table I. Arquad and Ethoquad™ are trademarks of Akzo Nobel Chemicals Inc. Kemamine™ is a trademark of Humko Chemical Division, Witco Corporation.

TABLE I

| Anticaking Agent | Amount of Anticaking Agent (ppm based on polymer) | Non-caking percent (%) | Moisture Level Percent (%) | Amount of Dust (ppm based on polymer) | Fluid Surface Tension (dynes/cm) |
|---|---|---|---|---|---|
| CONTROL | 0.000 | 0.00% | 24.60% | 53. | 66.2 |
| ARQUAD ™ 2C-75(1) | 1000 | 99.84% | 22.00% | 0.42 | 65.2 |
| ETHOQUAD ™ T/12–75(2) | 1000 | 99.07% | 28.40% | 0.68 | 65.1 |
| ETHOQUAD ™ O/12(3) | 1000 | 99.38% | 30.00% | 7.8 | 67.0 |
| ARQUAD ™ 12–33(4) | 1000 | 89.59% | 23.00% | 2.6 | 64.9 |
| ARQUAD ™ 16–50(5) | 1000 | 100.00% | 24.60% | 3.3 | 61.9 |
| ARQUAD ™ 18–50(6) | 1000 | 99.84% | 25.00% | 4.7 | 68.0 |
| ARQUAD ™ S-50(7) | 1000 | 97.22% | 29.60% | 0.091 | 65.3 |
| ARQUAD ™ S-50(7) | 1000 | 96.76% | 29.60% | 0.45 | 63.2 |
| Kemamine ™ Q2983-C(8) | 1000 | 99.03% | 24.20% | 0.23 | 69.7 |
| Kemamine ™ Q2983-C(8) | 300 | 100.00% | 20.20% | 9.1 | 66.4 |
| ARQUAD ™ 12-37W(9) | 1000 | 100.00% | 21.20% | 0.50 | 62.4 |
| ARQUAD ™ 12-37W(9) | 750 | 99.83% | 20.20% | 0.16 | 62.6 |
| ARQUAD ™ 12-37W(9) | 500 | 99.83% | 19.40% | 0.53 | 63.6 |
| ARQUAD ™ T-27W(10) | 1000 | 100.00% | 21.60% | 0.31 | 62.9 |
| ARQUAD ™ T-27W(10) | 750 | 99.67% | 20.80% | 1.3 | 62.1 |
| ARQUAD ™ T-27W(10) | 500 | 99.67% | 20.60% | 0.53 | 63.4 |
| 5% Active ARQUAD ™ 2HT-75PG in H$_2$O (11) | 1000 | 85.99% | 25.60% | 0.54 | 68.2 |
| ARQUAD ™ 2HT-75PG(11) | 1000 | 99.50% | 20.20% | 0.89 | 63.3 |
| ARQUAD ™ HTL8-MS(12) | 1000 | 100.00% | 24.80% | 0.094 | 68.1 |
| ARQUAD ™ HTL8-MS(12) | 300 | 77.13% | 26.80% | 13. | 66.2 |
| ARQUAD ™ HTL8-MS(12); 600 ppm Mineral Oil Added | 1000 | 99.84% | 25.40% | 0.25 | 64.0 |
| ARQUAD ™ HTL8-MS(12); 600 ppm Mineral Oil Added | 300 | 100.00% | 21.40% | 0.145 | 65.9 |
| Kemamine ™ Q9702-C(13) | 1000 | 98.72% | 25.20% | 0.11 | 62.9 |
| 2% of 5% Active Q9702-C ™ (13) in H$_2$O | 1000 | 99.83% | 20.00% | 0.65 | 62.7 |

TABLE I-continued

| Anticaking Agent | Amount of Anticaking Agent (ppm based on polymer) | Non-caking percent (%) | Moisture Level Percent (%) | Amount of Dust (ppm based on polymer) | Fluid Surface Tension (dynes/cm) |
|---|---|---|---|---|---|
| Kemamine ™ Q2802-C(14) | 1000 | 96.72% | 22.00% | 0.095 | 63.3 |
| 2% of 5% Active Q2802-C ™ (14) in $H_2O$ | 1000 | 100.00% | 20.40% | 0.56 | 63.1 |

TABLE IA

DESCRIPTION OF QUATERNARY SURFACTANTS

| | PRODUCT NAME | COMMON NAME OF QUATERNARY SURFACTANT |
|---|---|---|
| (1) | Arquad ™ 2C-75 | Di(cocoalkyl)dimethyl quaternary ammonium chloride |
| (2) | Ethoquad ™ T/12-75 | Tallowalkylmethyl di(2-hydroxyethyl) ammonium chloride |
| (3) | Ethoquad ™ O/12 | Oleylmethyldi(2-hydroxyethyl) ammonium chloride |
| (4) | Arquad ™ 12-23 | Dodecyltrimethyl ammonium chloride |
| (5) | Arquad ™ 16-50 | Hexadecyltrimethyl ammonium chloride |
| (6) | Arquad ™ 18-50 | Octadecyltrimethyl ammonium chloride |
| (7) | Arquad ™ S-50 | Soyaalkyltrimethyl ammonium chloride |
| (8) | Kemamine ™ Q-2983-C | Erucyltrimethyl ammonium chloride |
| (9) | Arquad ™ 12-37W | Dodecyltrimethyl ammonium chloride |
| (10) | Arquad ™ T-27W | Tallowalkyltrimethyl ammonium chloride |
| (11) | Arquad ™ 2HT-75PG | Di(hydrogenated tallowalkyl)dimethyl quaternary ammonium chloride |
| (12) | Arquad ™ HTL8-MS | 2-Ethylhexylhydrogenatedtallow-trimethyl ammonium methyl sulfate |
| (13) | Kemamine ™ Q-9702-C | Di(hydrogenated tallowalkyl)dimethyl quaternary ammonium chloride |
| (14) | Kemamine ™ Q-2802-C | Dibehenyldimethyl ammonium chloride |

EXAMPLE TWO

A test is conducted to examine the non-caking percent, moisture level in percent, and dustiness of water-swellable polymers and the surface tension of a liquid in contact with said polymers.

A water-swellable polymer is obtained which has been dried to about 5 to moisture. The polymer is DRYTECH™ 2035 superabsorbent (available from The Dow Chemical Company), a heat-treated, 62 percent neutralized polyacrylate. The polymer is heated to 50° C. in a 3-liter twin shaft, counter-rotating, batch paddle blender. Agitation is started and a predetermined amount of anticaking agent and/or dedusting agent, as shown in Table II, the anticaking agent being dissolved in the dedusting agent except where indicated, is sprayed on the polymer using an air atomizing nozzle. Agitation is continued until the mixture is non-cohesive, from about 2 to about 15 minutes. The non-caking percent and moisture level in percent is measured as described in the Caking Test above. The amount of dust below 10 microns is measured as described in the Dust Test above. The surface tension is measured as described in the Surface Tension Test above. The results with respect to each sample is set forth in Table II. In Table II, Q9702C represents Kenamine™ Q9702-C, Q2802C represents Kenamine™ 2802-C, Voranol represents Voranol 2070™ polyether polyol available from The Dow Chemical Company, and MO represent mineral oil.

TABLE II

| Anticaking Agent | Anticaking Agent (ppm based on polymer) | Dedusting Agent | Dedusting Agent (ppm based on polymer) | Added Water (%) | Non-caking percent (%) | Moisture Level Percent (%) | Amount of Dust (ppm based on polymer) | Surface Tension (dynes/cm) |
|---|---|---|---|---|---|---|---|---|
| none | 0 | none | 0 | 0 | 0.15 | 33.60 | 55. | 67.7 |
| none | 0 | Voranol | 700 | 2.5 | 0.00 | 34.40 | 0.018 | 63.2 |
| Q9702C (1) | 1000 | Voranol | 334 | 2.5 | 100.0 | 33.40 | 0.14 | 65.1 |
| Q9702C (1) | 500 | Voranol | 167 | 2.5 | 100.00 | 32.40 | 0.53 | 68.6 |
| Q9702C (1) | 200 | Voranol | 67 | 2.5 | 97.12 | 32.00 | 1.6 | 68.9 |
| Q9702C (1) | 100 | Voranol | 33 | 2.5 | 99.85 | 33.40 | 6.8 | 70.1 |
| Q9702C (1) | 100 | Voranol/MO | 400/33 | 2.5 | 99.51 | 22.40 | 1.3 | 66.8 |
| Q9702C (1) | 100 | Voranol | 433 | 2.5 | 99.17 | 21.20 | 0.16 | 68.2 |
| none | 0 | none | 0 | 0 | 0.59 | 35.80 | 22. | 70.5 |
| none | 0 | Voranol | 600 | 3 | 1.04 | 35.00 | 0.12 | 61.7 |
| Q2802C (2) | 1000 | Voranol | 334 | 2.5 | 99.09 | 32.40 | 0.061 | 66.3 |
| Q2802C (2) | 500 | Voranol | 167 | 2.5 | 83.43 | 34.00 | 1.5 | 68.1 |
| Q9702C (1) | 100 | Voranol | 500 | 3 | 99.70 | 33.80 | 0.55 | 64.5 |
| Q9702C (1) | 150 | Voranol | 450 | 3 | 99.70 | 34.40 | 0.8 | 66.9 |

(1) Di(hydrogenated tallow alkyl)dimethyl quaternary ammonium chloride
(2) Dibehenyldimethyl ammonium chloride The anticaking absorbent polymers of the examples exhibit centrifuge capacities and absorbences under load (AUL) similar to untreated absorbent polymers. In view of the description and examples, other embodiments will be readily ascertained by one having skill in the art. Accordingly, the scope of the invention shall be limited only by the claims set forth below.

What is claimed is:

1. A non-dusty, anti-caking composition comprising:
   a) water-absorbent lightly crosslinked water-insoluble polymer particles;
   b) an effective amount of a cationic surfactant anti-caking agent; and
   c) from about 100 ppm to about 6000 ppm based on the weight of the polymer particles of a hydrophilic dedusting agent.

2. A non-dusty, anti-caking composition comprising:
   a) water-absorbent lightly crosslinked water-insoluble polymer particles;
   b) an effective amount of a cationic surfactant anti-caking agent; and
   c) from 100 ppm to 3000 ppm based on the weight of the polymer particles of a hydrophilic dedusting agent.

3. The composition of claims 1 or 2 wherein the anticaking agent is represented by the formula 1:

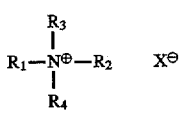

wherein $R_1$ and $R_3$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; $R_2$ is a $C_1$–$C_6$ aliphatic hydrocarbon or a phenyl group; and $R_4$ is a $C_1$–$C_{22}$ aliphatic hydrocarbon, a $C_1$–$C_4$ aliphatic hydrocarbon substituted with an unsubstituted aryl, or a $C_1$–$C_4$ aliphatic hydrocarbon substituted with an aryl group substituted with a $C_1$–$C_{22}$ aliphatic hydrocarbon, or $R_4$ is a radical represented by the formula 2:

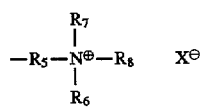

wherein $R_5$ is a $C_2$–$C_6$ alkylene group; $R_6$ is a $C_1$–$C_6$ aliphatic hydrocarbon or a phenyl group; $R_7$ and $R_8$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; or $R_2$ and $R_4$ taken together with the nitrogen atom forms a ring selected from the group consisting of pyrrolidine, pyrroline, pyrrole, pyrazole, triazole, indole, piperazine, piperidine, morpholine, and hexahydroazepine; or $R_1$, $R_2$, and $R_4$ taken together form a ring selected from the group consisting of pyridinium and imidazolinium; and $X^\ominus$ is an anion; with the provisos that if $R_4$ is not the radical represented by formula 2 then the sum of the carbons in $R_1$, $R_2$, $R_3$, and $R_4$ must be at least 15 and if $R_4$ is the radical represented by formula 2 then at least one of $R_1$, $R_3$, $R_7$, and $R_8$ must have 8 or more carbon atoms.

4. The composition of claim 3 wherein the anticaking agent is dihydrogenated tallow dimethyl ammonium chloride.

5. The composition of claim 2 wherein the composition comprises:
   a) water-absorbent lightly crosslinked water-insoluble polymer particles;
   b) from about 60 ppm to about 150 ppm, based on the weight of the polymer particles, of dihydrogenated tallow dimethyl ammonium chloride; and
   c) from about 400 ppm to about 600 ppm, based on the weight of the polymer particles, of a polyether polyol.

6. An absorbent article prepared from the composition of claims 1 or 2.

7. A process comprising:
   a) preparing a water-swellable hydrogel by a gel polymerization process;
   b) drying and sizing the thus prepared hydrogel to obtain a composition comprising dried and sized particles; and
   c) contacting the composition with an effective amount of a cationic surfactant anti-caking agent and from about 100 ppm to 6,000 ppm of a hydrophobic dedusting agent, under conditions sufficient to physically coat the particles with the anti-caking agent and the dedusting agent.

8. The process of claim 7 wherein the composition is heat treated before contacting the composition with the anticaking agent.

9. The process of claims 7 wherein the anticaking agent is represented by the formula 1:

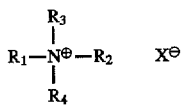

wherein $R_1$ and $R_3$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; $R_2$ is a $C_1$–$C_6$ aliphatic hydrocarbon or a phenyl group; and $R_4$ is a $C_1$–$C_{22}$ aliphatic hydrocarbon, a $C_1$–$C_4$ aliphatic hydrocarbon substituted with an unsubstituted aryl, or a $C_1$–$C_4$ aliphatic hydrocarbon substituted with an aryl group substituted with a $C_1$–$C_{22}$ aliphatic hydrocarbon, or $R_4$ is a radical represented by the formula 2:

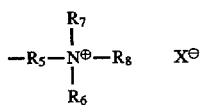

wherein $R_5$ is a $C_2$–$C_6$ alkylene group; $R_6$ is a $C_1$–$C_6$ aliphatic hydrocarbon or a phenyl group; $R_7$ and $R_8$ are independently a $C_1$–$C_{22}$ aliphatic hydrocarbon, a $C_1$–$C_4$ aliphatic hydrocarbon substituted with an unsubstituted aryl group, a $C_1$–$C_4$ aliphatic hydrocarbon substituted with an aryl group substituted with a $C_1$–$C_{22}$ aliphatic hydrocarbon, or a phenyl group; or $R_2$ and $R_4$ taken together with the nitrogen atom forms a ring selected from the group consisting of pyrrolidine, pyrroline, pyrrole, pyrazole, triazole, indole, piperazine, piperidine, morpholine, and hexahydroazepine; or $R_1$, $R_2$, and $R_4$ taken together form a ring selected from the group consisting of pyridinium and imidazolinium; and $X^\ominus$ is an anion; with the provisos that if $R_4$ is not the radical represented by formula 2 then the sum of the carbons in $R_1$, $R_2$, $R_3$, and $R_4$ must be at least 15 and if $R_4$ is the radical represented by formula 2 then at least one of $R_1$, $R_3$, $R_7$, and $R_8$ must have 8 or more carbon atoms.

10. An absorbent article comprising from about 5 to about 90 percent by weight of a superabsorbent polymer composition according to claims 1 or 2 and about 10 to about 95 percent by weight of a hydrophilic fiber.

11. An absorbent article comprising from about 30 to about 90 percent by weight of a superabsorbent polymer composition according to claims 1 or 2 and about 10 to about 70 percent by weight of a hydrophilic fiber.

12. An absorbent article comprising from about 30 to about 70 percent by weight of a superabsorbent polymer composition according to claims 1 or 2 and about 30 to about 70 percent by weight of a hydrophilic fiber.

\* \* \* \* \*

UNITED STATES PATENT AND TRADEMARK OFFICE
CERTIFICATE OF CORRECTION

PATENT NO : 5,728,742

DATED : March 17, 1998

INVENTOR(S) : Thomas L. Staples; David E. Henton; Gene D. Rose; Michael A. Fialkowski It is certified that error appears in the above-identified patent and that said Letters Patent is hereby corrected as shown below:

Col. 17, line 15, "hydrophilic" should read -- hydrophobic --.

Col. 18, line 25, "claims" should read -- claim --.

Col. 18, line 61, "provisos" should read -- proviso --.

Signed and Sealed this

Second Day of May, 2000

Attest:

Q. TODD DICKINSON

*Attesting Officer*  *Director of Patents and Trademarks*